United States Patent [19]

Siegmund et al.

[11] Patent Number: 4,902,129

[45] Date of Patent: Feb. 20, 1990

[54] ORIENTATION INDICATOR FOR A FLEXIBLE FIBERSCOPE OR ENDOSCOPE INCLUDING METHOD OF MANUFACTURE

[75] Inventors: Walter P. Siegmund, Windham, Conn.; Anthony F. Szwarc, Sturbridge, Mass.

[73] Assignee: Schott Fiber Optics, Southbridge, Mass.

[21] Appl. No.: 240,501

[22] Filed: Sep. 6, 1988

[51] Int. Cl.$^4$ .................. G02B 23/26; G01C 9/20
[52] U.S. Cl. ........................ 356/241; 33/377; 128/6; 350/96.26; 356/249
[58] Field of Search ............ 356/241, 248, 249; 350/96.26; 128/6; 33/377

[56] References Cited

U.S. PATENT DOCUMENTS

| | | | |
|---|---|---|---|
| 3,088,216 | 5/1963 | Jesonis | 356/249 X |
| 3,525,561 | 8/1970 | Takahashi | 356/241 X |
| 3,891,328 | 6/1975 | Hall et al. | 356/249 |
| 4,277,168 | 7/1981 | Oku | 356/241 X |
| 4,641,434 | 2/1987 | Engler | 33/377 X |
| 4,745,908 | 5/1988 | Wardle | 128/6 |

Primary Examiner—Vincent P. McGraw
Attorney, Agent, or Firm—Bachman & LaPointe

[57] ABSTRACT

An orientation indicator is disclosed for observing or reading the orientation of the distal end of an endoscope or of a fiberscope having an elongated flexible shaft relative to the proximate end thereof where the flexible shaft the fiber optic bundles of the scope are subject to torque or rotational stresses. The disclosure includes a method of making the orientation indicator and means for measuring the degree and direction of displacement resulting from said rotational stress or torque.

4 Claims, 2 Drawing Sheets

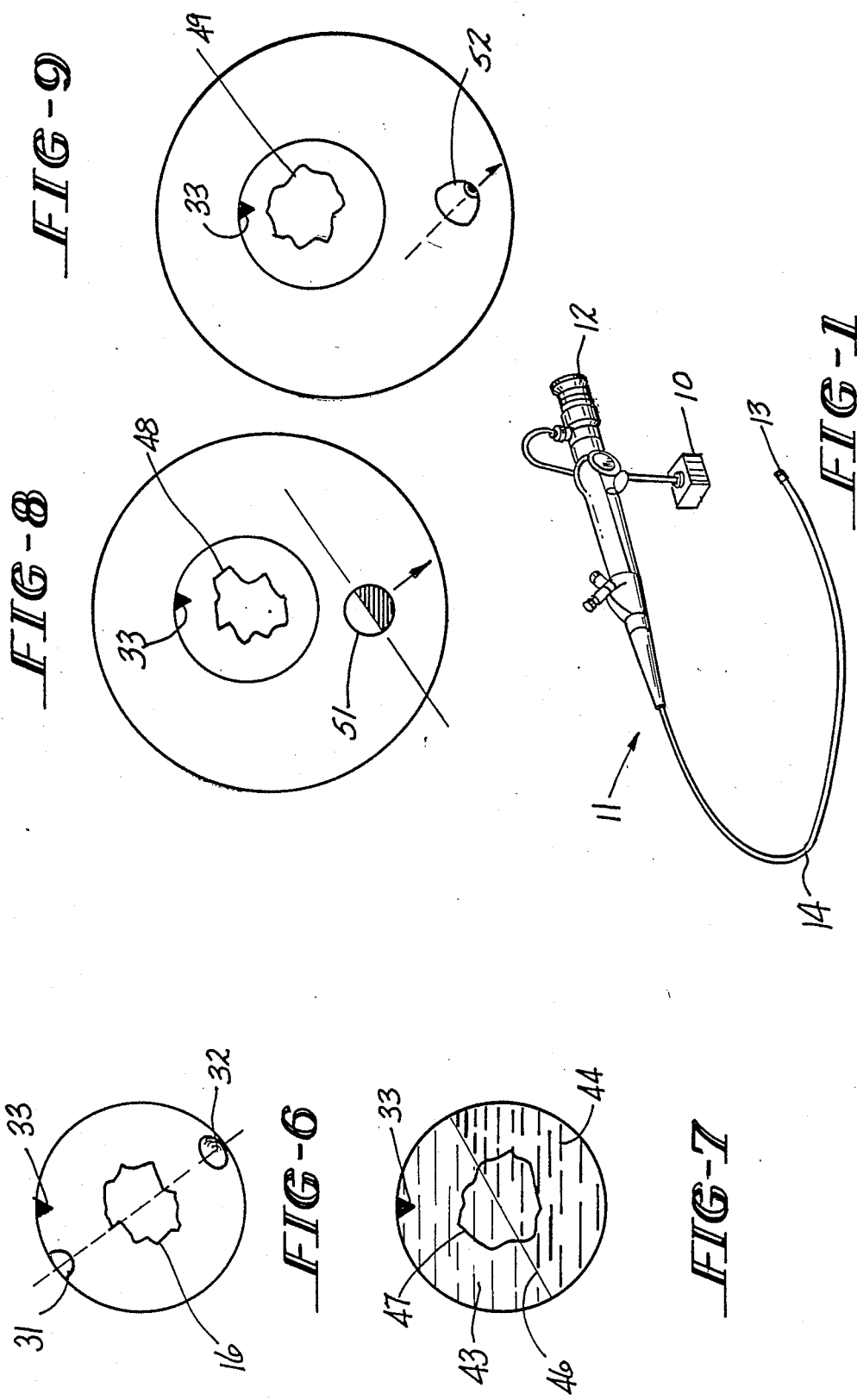

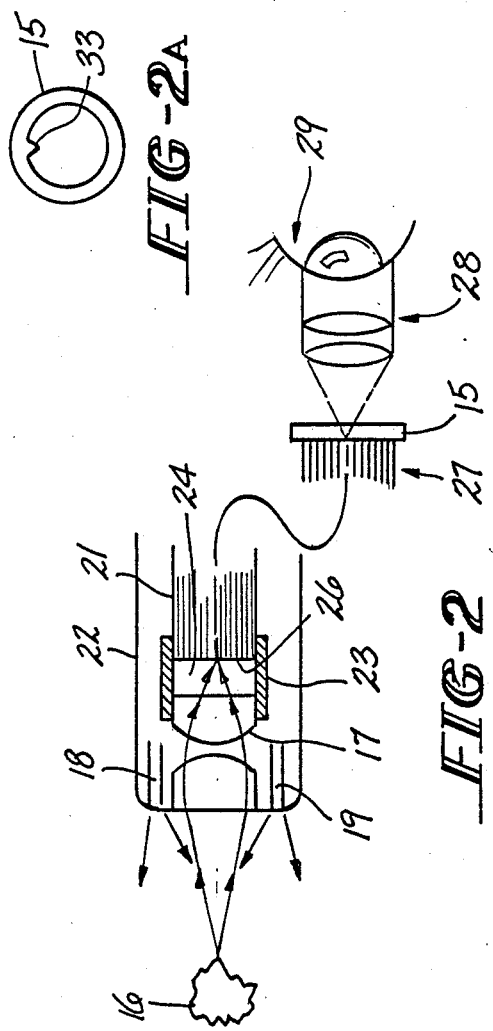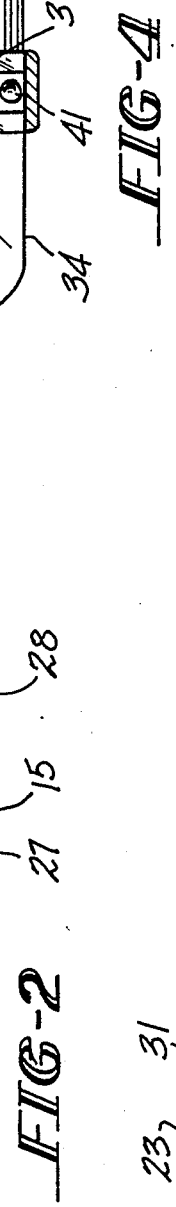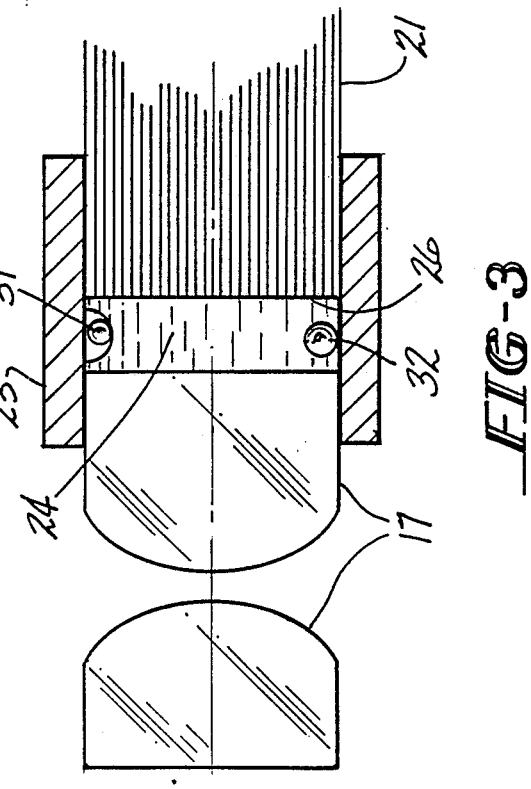

ORIENTATION INDICATOR FOR A FLEXIBLE FIBERSCOPE OR ENDOSCOPE INCLUDING METHOD OF MANUFACTURE

BACKGROUND OF THE INVENTION

The present invention relates to endoscopes or fiberscopes and, in particular, relates to such scopes having elongated flexible fiber optic bundles for imaging and illuminating remote objects in medical, veterinary, and industrial applications.

Representative examples of prior art scopes are shown and described in U.S. Pat. Nos. 4,277,168 and 4,745,908 issued Jul. 7, 1981 and May 24, 1988 to Toshio Oka and John L. Wardle, respectively.

The '168 patent deals with a mechanical device 12—12 connected to Wires 11—11 for positively twisting the distal end 1 of a flexible sheath 2 relative to a grip end 3. By means of a fixed guide tube 9 with an internal mark 16, the direction and angle of rotation of the distal end relative to the guide tube are detected optically to avoid damage at the distal end because of excessive torquing.

The '908 patent shows a scope with a wire braid sheath 67 for torque stabilizing so as to maintain registering between control head 4 and objective head 6.

While the above devices are operative, they do not show or suggest elongated flexible fiber optic bundles free to rotate to any degree in response to torque or twisting stresses with subtle or ingenious means incorporated into a distal end of a scope for indicating very clearly the rotational orientation of the distal end of the scope relative to a known bench mark or pointer.

SUMMARY OF THE INVENTION

Thus, it is a primary feature of the present invention to provide a simple inexpensive means for readinq the attitude of a remote object relative to a known reference, datum, pointer or bench mark independently of the degree or direction of rotation of the distal end of a fiberscope shaft relative to the proximal end thereof.

A further feature of the invention is the provision of means at the distal end of a fiberscope observable at the proximate end of the scope for indicating the orientation of the distal end of the scope relative to a known spatial reference.

A still further feature of the invention is the provision of means at the distal end of a flexible fiber optic bundle observable at the proximate end thereof for indicating true vertical or true horizontal.

A further feature of the invention is the provision of a flexible fiber optic shaft including an image bundle and a light bundle for observing a remote object where the distal end includes an orientation device or indicator means which is observable at the proximate end of the shaft via the same image bundle through which the object is observed.

A further feature of the invention is the provision of a flexible fiber optic shaft of the above type having a first image bundle for observing a remote object and a second image bundle for observing the orientation device; both image bundles being observable through a common eye piece at the proximate end of the shaft.

A further feature of the invention is the provision of a reticle, pointer or bench mark on an eye piece for indicating the degree of rotational orientation of the distal end of a flexible fiber optic shaft relative to the proximate end.

A further feature of the invention is the provision of an indicator means at the distal end of flexible fiber optic bundles including an image bundle and a light bundle where the indicator means is in the form of a cell containing a bubble in a liquid.

A further feature of the invention is the inclusion in said cell of a race providing a track for a small sphere or pellet.

A still further feature of the invention is the provision of a cell containing two immiscible fluids, each of a different specified gravity.

A further feature of the invention is the provision of a novel method of determining the orientation or attitude of the distal end of a flexible fiber optic shaft relative to the proximal end thereof.

An orientation indicator for a flexible fiberscope or endoscope embracing certain principles of the present invention may comprise a first elongated fiber optic image bundle for observing a remote object, at least one fiber optic light bundle for illuminating said object, both said bundles being subject to torque or twisting stresses, observation means at a proximate end of said image bundle for viewing said object, and means at a distal end of said image bundle, observable via said observation means, for indicating the rotational orientation of said distal end relative to said proximate end of said bundles.

A method of determining the rotational orientation of the distal end of a fiberscope, including fiber optic bundles, relative to the proximal end thereof as a result of twisting stress may comprise the step of incorporating an indicator means at the distal end of the scope for indicating the rotational orientation of said bundles resulting from said stress, viewing said indicator means at the proximate end of said bundles, and comparing the rotational orientation of the indicator means relative to a bench mark or a pointer.

Other features and advantages of the present invention will become more apparent from an examination of the succeeding specification when read in conjunction with the appended drawings, in which:

BRIEF DESCRIPTION OF THE DRAWINGS

FIG. 1 is a perspective view of a typical endoscope or fiberscope embracing the principles of the present invention;

FIG. 2 is a fragmentary view of a typical distal end and eye piece of an endoscope with the main body of the fiber optic bundles removed and broken away;

FIG. 2a is a front elevation of a portion of the eye piece showing a mask with a pointer or bench mark.

FIG. 3 is a view of the distal end portion of FIG. 2, enlarged and with the light bundles removed illustrating two embodiments of the orientation indicator;

FIG. 4 is an alternative embodiment of the orientation indicator;

FIG. 5 is a still further embodiment of the orientation indicator including a fiber optic face plate;

FIGS. 6 and 7 are typical views observed through the eye piece of an endoscope including the object, eye piece reticle or pointer and different embodiments of the orientation indicator where the orientation indicators and the object are both viewed through the same image bundle; and FIGS. 8 and 9 illustrate the view of the object and the orientation indicator as observed at the proximate end of the scope where the object and the indicator means are transmitted by individual image bundles.

DETAILED DESCRIPTION

Referring now to the drawings, reference numeral 11 indicates an endoscope or fiberscope, generally, having light source 10, eye piece 12 at the proximate end thereof and objective head 13 at the distal end joined by a sheathed, flexible fiber optic bundle 14.

While it is not critical to the understanding of the present invention, it is usual and customary that the sheathed fiber optic bundle include additional openings or passageways for fluids, vacuum and/or biopsy and tip deflecting means in the usual and customary way.

A distal or object end of a scope embracing principles of the present invention is shown at FIG. 2 including an object 16, a lens pack 17, light bundles 18 and 19, image bundle 21, and sheath 22 enclosing a sealing ring 23 defining a cell 24 between the bitter end 26 of the image bundle and the lens pack.

The proximate end of the imaqe bundle, indicated generally by the reference numeral 27, includes an eye piece 28 with the representatiOn with the eye of an observer 29.

The eye piece includes a mask or ring 15 having a pointer or bench mark 33 normally indicating a known reference, such as vertical at the proximal end of the scope.

Referring now to FIG. 3, an enlarged view of a portion of FIG. 2 shows sealing ring 23 receiving a portion of the lens pack 17 at one end and the bitter end 26 of image bundle 21 at the other end. Void or cell 24 shows two embodiments of an orientation indicator, both observable through the eye piece 28 via the image bundle 21, which also transmits the representation of object 16.

In one embodiment of the orientation indicator of FIG. 3, the cell 24 is filled with liquid, such as alcohol supporting a bubble or float 31 in the manner that such a bubble or float is incorporated in a conventional carpenter's level.

The other embodiment of the orientation indicator of FIG. 3 can take the form of a ball 32, such as a small metallic or ceramic sphere, in air or liquid, where the internal diameter of the sealing ring serves as a race for the ball.

Thus, in the float or bubble embodiment of the orientation indicator, the bubble or float will always indicate the horizontal. Therefore, even though the observer at the eye piece 28 looking at object 16, as in FIG. 6, observes a bubble or float 31 at approximately 11 o'clock relative to fixed bench mark or pointer 33 at 12 o'clock, the observer is certain the bubble 31 indicates true vertical or "up" with respect to the surroundings of object 16.

Correspondingly, the observer is certain that ball or sphere 32, while appearing at approximately 5 o'clock (FIG. 6), actually represents true vertical or "down".

Therefore, it is apparent that no matter what degree of rotary or twisting distortion occurs in the fiber optic bundles between the eye piece and the objective head the observer is certain that float 31 represents up and the ball 32, by virtue of gravity, represents down.

Obviously, the orientation indicator need not include both the float 31 and the ball 32. One or the other is adequate to indicate true vertical in that the ball always indicates which direction is vertical or down and the float in corresponding fashion indicates the vertical or up direction.

As is further apparent in FIG. 6, it is emphasized that the orientation indicator can be arranged so that one image bundle permits the viewer to observe both the object and the indicator simultaneously.

FIGS. 4 and 5 show modifications in which the indicator means includes a lens 34, sealing ring 36, cavity 37 straddled by glass plates 38 and 39.

In this embodiment, the cell 37 is filled with air and the orientation indicator comprises a ball 41 solely.

FIG. 5 is similar to FIG. 4 with the substitution of a fiber optic face plate 42 for plain glass 39 (FIG. 4).

Alternative to providing a ball subject to gravity or a float or a bubble in the manner of a carpenter's level, the orientation means can take the form of two immiscible liquids 43 and 44, as indicated in FIG. 7 where one liquid, such as liquid 44, is of greater specific gravity than liquid 43 so that in the normal, at rest situation, the line of demarcation between the two liquids represents the horizontal, as indicated by the reference numeral 46 in FIG. 7.

For additional convenience, it is recommended that the two immiscible liquids of different gravities be tinted with contrasting colors so that an observer seeing object 47 has a clear representation of the line 46 indicating horizontal.

FIGS. 8 and 9 are representations of an observer's view where the objects 48 and 49 are transmitted by a first image bundle and the indicator means indicia 51 and 52 are transmitted to the same eye piece by a second image bundle. Therefore, the object and the indicator means each have their own individual image bundles both of which are observed through a single eye piece.

It is anticipated that a wide variety of indicator means may be devised showing the directions "up", "down" or "horizontal" without departing from the spirit and scope of the invention.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An orientation indicator for a flexible fiberscope or an endoscope comprising:
   a first elongated fiber optic image bundle for observing a remote object,
   at least one fiber optic light bundle for illuminating said object,
   both said bundles being subject to torque or twisting stresses,
   observation means at a proximate end of said image bundle for viewing said object, and,
   indicator means at a distal end of said image bundle, observable via said observation means, for indicating the rotational orientation of said distal end relative to said proximate end of said bundles, said indicator means defining a cell containing two immiscible fluids, each fluid having a different color and a different specific gravity whereby the line of demarcation between the two fluids is visible clearly.

2. The orientation indicator of claim 1 including a second elongated image bundle for transmitting an image of said indicator means independently of said first image bundle.

3. The orientation indicator of claim 2 in which the object and the indicator means are both viewed at said observation means.

4. The orientation indicator of claim 1 in which the observation means defines an eye piece for viewing the object and the indicator means simultaneously.

* * * * *